United States Patent [19]

Hester, Jr.

[11] 4,018,788
[45] Apr. 19, 1977

[54] 6-(O-HALOPHENYL)-1-METHYL-4H-S-TRIAZOLO[4,3-a][1,4]-BENZODIAZEPINE

[75] Inventor: Jackson B. Hester, Jr., Galesburg, Mich.

[73] Assignee: The Upjohn Company, Kalamazoo, Mich.

[22] Filed: Dec. 24, 1975

[21] Appl. No.: 644,368

Related U.S. Application Data

[63] Continuation of Ser. No. 586,959, June 16, 1975, abandoned, which is a continuation of Ser. No. 496,219, Aug. 9, 1974, abandoned, which is a continuation of Ser. No. 361,481, May 18, 1973, abandoned, which is a continuation of Ser. No. 120,760, March 3, 1977, abandoned.

[52] U.S. Cl. .................. 260/308 R; 260/239 BD; 260/239.3 B; 424/269
[51] Int. Cl.$^2$ ........................... C07D 487/12
[58] Field of Search ................ 260/308 R

[56] References Cited

UNITED STATES PATENTS 3,681,343  8/1972  Hester .................. 260/308 R

FOREIGN PATENTS OR APPLICATIONS 2,164,778  10/1972  Germany ............... 260/308 R
6,916,543  5/1970  Netherlands ........... 260/308 R

OTHER PUBLICATIONS

Sternbach et al., Symposium on CNS Drugs., Hyderabad, India, CSIR (New Delhi, India, 1966), p. 11 of reprint.
Kuwada et al., C. A. 83, 97403h, (1975)–Abstract of Japan. Patent 75–18,498 of 2–75.

*Primary Examiner*—Raymond V. Rush
*Attorney, Agent, or Firm*—Hans L. Berneis; Willard L. Cheesman

[57] ABSTRACT

6-(o-halophenyl)-1-methyl-4H-s-triazolo[4,3-a][1,4]-benzodiazepines of the following formula:

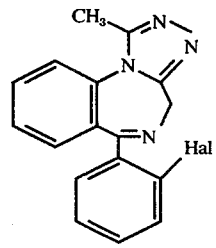

I wherein the substituent "Hal" is either of the halogens having an atomic number up to 35, inclusive, i.e., fluoro, chloro or bromo, and their pharmacologically acceptable acid addition salts which are especially useful as muscle relaxing and anxiolylic agents.

4 Claims, No Drawings

6-(O-HALOPHENYL)-1-METHYL-4H-s-TRIAZOLO[4,3-a][1,4]-BENZODIAZEPINE

CROSS-REFERENCES TO OTHER APPLICATIONS

This application is a continuation of application Ser. No. 586,959 filed June 16, 1975, which is a continuation of application Ser. No. 496,219, filed Aug. 9, 1974, which is a continuation of application Ser. No. 361,481, filed May 18, 1973, which is a continuation of application Ser. No. 120,760, filed March 3, 1971, all of which are now abandoned.

BACKGROUND OF THE INVENTION

Field of the Invention

The novel compounds of this invention can be made by the following process:

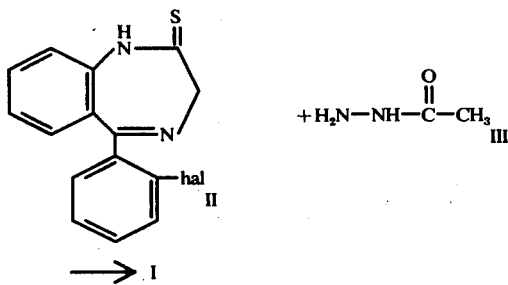

The process comprises condensing II with III in an organic solvent, e.g., a lower alkanol of 1 to 4 carbon atoms, inclusive, or a cycloalkanol such as cyclohexanol, at a temperature of 60° to 120° C. to give I. The reaction takes a course through the intermediate open chain compound:

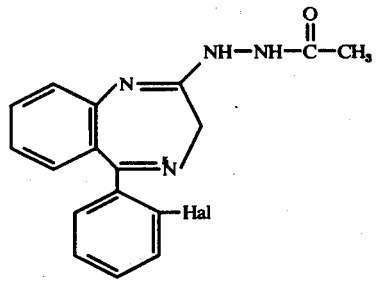

This intermediate compound is not necessarily isolated, nor is the formation of it necessarily a distinct phase of the process. Under vigorous reaction conditions such as, for example prolonged reaction times and elevated temperatures, the final product I is obtained predominately. IV can be regarded as a partially condensed product, and it can be separated from I by conventional methods such as extraction, chromatography, crystallization and the like, and can be put to pharmacological use, per se, as it possesses properties as a sedative, tranquilizer and muscle relaxant in mammals and birds, or it can be converted by further condensation to I by heating, say, to the melting point. Alternatively a mixture of I and IV such as can be obtained as above, can be heated to, say, the melting point to convert IV to I. I in free base form or in the form of its salts, can be used in treating mammals and birds in the same way that known muscle relaxants such as diazepam or mephenes in are used, with due regard to appropriate adjustment of dosages to the activity of I.

BRIEF DESCRIPTION OF THE INVENTION

The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies and the like. Suitable diluents or carriers such as carbohydrates (lactose), proteins, lipids, calcium phosphate, cornstarch, stearic acid, methylcellulose and the like can be used as carriers or for coating purposes. Oil, e.g., coconut oil, sesame oil, safflower oil, cottonseed oil, peanut oil can be used for preparing solution or suspensions of the active drug. Sweetening, coloring and flavoring agents can be added.

For mammals and birds food premixes, with starch, oatmeal, dried fishmeat, fishmeal, flour and the like can be prepared.

As muscle relaxants, the compounds of formula I and their pharmacologically acceptable acid addition salts can be used in dosages of 0.01 mg.-2.0 mg./kg. in oral or injectable preparations. They can be used to alleviate muscle cramps in pets and domestic animals as occur, for example, after strenuous activity.

The starting materials of this invention are described by G. A. Archer and L. H. Sternbach [J. Org. Chem. 29,231 (1964) and U.S. Pat. No. 3,422,091]. These starting compounds are made by the reaction of the appropriate known 1,3-dihydro-5-(o-halophenyl)-2H-1,4-benzodiazepin-2-one by heating with phosphorus pentasulfide in pyridine for about 45 minutes (Archer et al., ibid.)

In carrying out the process of the invention, the starting material, in an inert organic solvent, preferably in a lower-alkanol, e.g., methanol, ethanol, 1-propanol, 2-propanol, 1-butanol, 2-butanol or the like is heated to between 60°-120° C., preferably to the reflux temperature of the mixture, with the acetic acid hydrazide $NH_2-NH-COCH_3$. In a preferred embodiment the acid hydrazide is used in excess, such as from 2 to 5 times the theoretically required amount, but the reaction is operative with smaller or larger amounts. The reaction period is between 1 and 48 hours. At the termination of the reaction the reaction mixture can be evaporated to give a crude product consisting of the desired I and the partially condensed compound, a 2-(2-acylhydrazino)-5-(o-halophenyl)-3H-1,4-benzodiazepine (IV), which can be separated from each other, usually by their different solubility in an organic solvent, e.g., methylene chloride, chloroform, carbon tetrachloride, ethyl acetate, mixtures thereof and the like. The compound IV after separation can be converted to compound I by heating it above its melting point for 1 to 10 minutes. In a more simple manner the crude mixture of compounds I and IV is heated to 200°-275° C., thereby converting all of compound IV to compound I. The crude compound I is then purified by standard methods, e.g., chromatography or recrystallization from solvents such as ethyl acetate, methylene chloride, chloroform, acetonitrile or the like.

To make the 6-(o-bromophenyl) product one can follow the procedure shown by Sternbach et al., J. Med. Chem. 6, 263 (1963), for the preparation of 1,3-dihydro-5-(o-chlorophenyl)-2H-1,4-benzodiazepin-2-one using the Sandmeyer reaction followed by catalytic hydrogenation of the resulting 2-bromo-2'- nitrobenzophenone. This product, 2-amino-2'-bromobenzophenone, can be substituted in the process described by Sternbach et al. to produce 1,3-dihydro-5-(o-bromophenyl)-2H-1,4-benzodiazepin-2-one.

DETAILED DESCRIPTION OF THE INVENTION

The following examples are illustrative of the processes and products of the present invention, but are not to be construed as limiting.

Preparation 1

1,3-Dihydro-5-(o-chlorophenyl)-2H-1,4-benzodiazepine-2-thione

A mixture of 23 g. (0.085 mole) of 1,3-dihydro-5-(o-chlorophenyl)-2H-1,4-benzodiazepin-2-one [Sternbach et al., J. Med. Chem. 6, 261 (1963)] and 21 g. of $P_2S_5$ in 1500 ml. of pyridine was heated rapidly to the reflux temperature and refluxed for 45 min. It was then concentrated to dryness in vacuo and the residue was treated with 150 ml. of saturated NaCl solution and extracted (thrice) with methylene chloride. The $CH_2Cl_2$ solution was washed (water), dried ($MgSO_4$), filtered and evaporated to dryness. The residue was dissolved in 1 l. of abs EtOH treated with Darco and filtered hot. The solution was then concentrated to 200 ml. and allowed to cool giving 19 g. (78%) of yellow crystalline compound, m.p. 228–229° C. The ir and nmr support the structure.

Anal. calcd. for $C_{15}H_{11}ClN_2S$: C, 62·94; H, 3·84; N, 9·79; Cl, 12·24; S, 11·19. Found: C, 62·29; H, 4·01; N, 9·43; Cl, 12·61; S, 11·12.

EXAMPLE 1

6-(o-chlorophenyl)-1-methyl-4H-s-triazolo[4,3-a][1,4]benzodiazepine

A mixture of 14 g. (0.05 mole) of 1,3-dihydro-5-(o-chlorophenyl)-2H-1,4-benzodiazepine-2-thione and 10 g. (0.13 mole) of acethydazide in 1400 ml. of n-BuOH was refluxed for 24 hrs. During this period $N_2$ was bubbled through the reaction mixture. This was then evaporated to dryness in vacuo and the residue was treated with water, which gave a yellow solid. This was collected and air dried, weight 12 g. The compound was crystallized by dissolving in 700 ml. of ethyl acetate and concentrating to 150 ml. and cooling giving 11 g. (73%) of white crystalline compound, m.p. 211.5°–213° C. This showed only one spot on TLC (10% $MeOH/CHCl_3$). The ir and nmr support the structure.

Anal. calcd. for $C_{17}H_{13}ClN_4$: C, 66·13; H, 4·24; N, 18·15; Cl, 11·48. Found: C, 66·08; H, 3·96; N, 18·24; Cl, 11·61.

EXAMPLE 2

6-(o-fluorophenyl)-1-methyl-4H-s-triazolo[4,3-a][1,4]benzodiazepine

A mixture of 1,3-dihydro-5-(o-fluorophenyl)-2H-1,4-benzodiazepin-2-one [Sternbach et al., J. Org. Chem. 27, 3788 (1962)] and $P_2S_5$ can be reacted in the same manner as in preparation I to produce 1,3-dihydro-5-(o-fluorophenyl)-2H-1,4-benzodiazepine-2-thione. This latter compound can then be substituted in the procedure of Exmple 1 to produce 6-(o-fluorophenyl)-1methyl-4H-s-triazolo[4,3-a][1,4] benzodiazepine.

EXAMPLE 3

6-(o-bromophenyl)-1-methyl-4H-s-triazolo-[4,3-a][1,4]benzodiazepin.

A mixture of 1,3-dihydro-5-(o-bromophenyl)-2H-1,4-benzodiazepin-2-one and $P_2S_5$ can be reacted in the same manner as in Preparation I to produce 1,3-dihydro-5-(o-bromophenyl)-2H-1,4-benzodiazepine-2-thione. This latter compound can then be substituted in the procedure of Example 1 to produce 6-(o-bromophenyl)-1-methyl-4H-s-triazolo[4,3-a][1,4]benzodiazepine.

I claim:
1. A compound of formula:

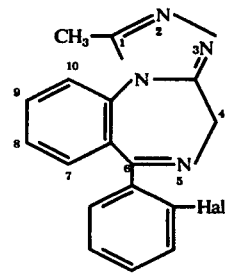

wherein Hal is a halogen having an atomic number up to 35, inclusive, and its pharmacologically acceptable acid addition salts.

2. The compound of claim 1, 6-(o-chlorophenyl)-1-methyl-4H-s-triazolo[4,3-a][1,4]benzodiazepine.
3. The compound of claim 1, 6-(o-fluorophenyl)-1-methyl4H-s-triazolo[4,3-a][1,4]benzodiazepine.
4. A compound of claim 1, 6-(o-bromophenyl)-1-methyl-4H-s-triazolo[4,3-a][1,4]benzodiazepine.

* * * * *